Figure 1:
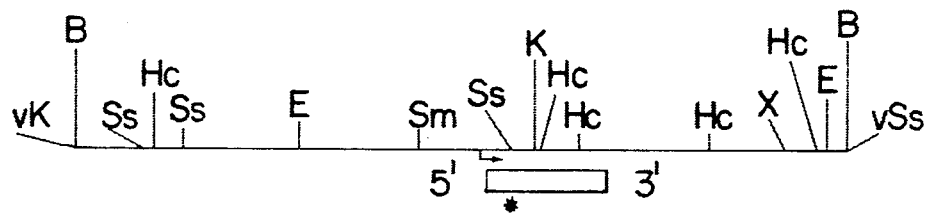

United States Patent [19]
Boston et al.

[11] Patent Number: 5,332,808
[45] Date of Patent: Jul. 26, 1994

[54] DNA ENCODING A RIBOSOME INACTIVATING PROTEIN

[75] Inventors: Rebecca S. Boston, Raleigh, N.C.; Henry W. Bass, Oakland, Calif.; Gregory R. OBrian, Raleigh, N.C.

[73] Assignee: North Carolina State University, Raleigh, N.C.

[21] Appl. No.: 941,651

[22] Filed: Sep. 8, 1992

[51] Int. Cl.⁵ .................. C07H 17/00; C12N 15/00
[52] U.S. Cl. .................. 536/23.6; 536/24.1; 435/172.3; 435/320.1
[58] Field of Search .................. 800/205, 200; 435/172.1, 172.3, 320.1; 536/23.2, 23.6, 24.3, 25.3, 24.1

[56] References Cited

FOREIGN PATENT DOCUMENTS

0466222A1 10/1991 European Pat. Off. ...... C07K 15/10
0466222   1/1992  European Pat. Off. ................ 15/10

OTHER PUBLICATIONS

Bass et al. 1992. Plant Cell 4:225–234.
Watson et al. 1987. p. 313 in: *Molecular Biology of the Gene*, 4th ed.
Hartings et al. 1990. Plant Mol. Biol. 14:1031–1040.
Di Fonzo et al. 1988. Mol. Gen. Genet. 212: 481–487.
Walsh et al. Dec. 1991. J. Biol. Chem. 266: 23422–23427.
Walsh et al., *Characterization and Molecular Cloning of a Proenzyme Form of a Ribosome-Inactivating Protein from Maize*, The Journal of Biological Chemistry, vol. 266, No. 34, pp. 23422–23427 (1991).
Bass et al., *A Maize Ribosome-Inactivating Protein is Controlled by the Transcriptional Activator Opaque-2*, The Plant Cell, vol. 4, pp. 225–234 (1992).

Primary Examiner—David T. Fox
Assistant Examiner—Elizabeth C. Kemmerer
Attorney, Agent, or Firm—Bell, Seltzer, Park & Gibson

[57] ABSTRACT

Isolated DNA for a ribosome-inactivating protein found in the tissues of Zea mays is disclosed. The invention also encompasses the protein itself, transgenic plants containing the DNA, DNA constructs for producing the protein, and a host cell containing the DNA.

5 Claims, 8 Drawing Sheets

```
1                              *              60
CCACTACATATATCTGCAACGAGCGCATCGCCAATTCACAATGCCAATTGCCAGCAACCC
61                                                           120
ATCCATACTTTCAGCTGTTGATACAAAAAGAGAAGAGAGAATGGCGGAGCCAAACCCAGA
                                         M A E P N P E
121                                                          180
GTTGAGTGGTCTTATTACTCAAACAAAGAAGAAAAATATAGTGCCAAAGTTCACCGAAAT
  L S G L I T Q T K K K N I V P K F T E I
181                                                          240
CTTCCCCGTGGAGGACACGGCCTACCCTTACAGCGCCTTCATCACCTCCGTCCGGAAAGA
  F P V E D T A Y P Y S A F I T S V R K E
241                                                          300
AGTGATCAAATACTGCACCAACCATACAGGCATCGTCCAGCCCGTGCTGCCGCTGGAGAA
  V I K Y C T N H T G I V Q P V L P L E K
301                                                          360
GAATGTCCCCGAGCTCTGGTTCTACACCGAGCTCAAAACGAAGACCAGGTCCATCACGCT
  N V P E L W F Y T E L K T K T R S I T L
361                                                          420
CGCCATACGTATGGACAACCTCTACCTGGTCGGCTTCAGGACCCCCGGCGGGGTGTGGTG
  A I R M D N L Y L V G F R T P G G V W W
421                                                          480
GGAGTTCGGCAAGGACGGCGACACCCACCTCCTCGACGACAACGCCAAGTGGCTCGGCTT
  E F G K D G D T H L L D D N A K W L G F
481                                                          540
TGGCGGCCGGTACCAGGACCTCATCGGCAGTAAGGGCCTGGAGACCGTCACCATGGGCCG
  G G R Y Q D L I G S K G L E T V T M G R
541                                                          600
TGCCGAAATGACCACGGCCGTCAACTACCTGGCGAAGAAGACGACGACGACACTAGCAGA
  A E M T T A V N Y L A K K T T T T L A E
601                                                          660
GGCGGCCGAGGAGGAGGAGGAGCTGCTGCTGCTGCAGGCAGCGGCTGACCCCAAAGCCGA
  A A E E E E L L L L Q A A A D P K A E
661                                                          720
GGAGAAGAGCAACCTGGCGAAGCTAGTGATCATGGTATGCGAGGGCCTGCGGTTCTTCAC
  E K S N L A K L V I M V C E G L R F F T
721                                                          780
CGTGTCCCGCAAGGTAGACGAGGGGTTCAAGAAGCCGCAAGCGGTGACCATATCGGCGCT
  V S R K V D E G F K K P Q A V T I S A L
781                                                          840
GGAGGGGAAGCAGGTGCAGAAATGGGACAGGATCTCGAAAGCCGTCTTCAGGTGGGCCGT
  E G K Q V Q K W D R I S K A V F R W A V
841                                                          900
CGACCCCGACCGCTGAGATCCCCGACATGAAGGATCTTGGCATCAAAGATAAAAACGCAGC
  D P T A E I P D M K D L G I K D K N A A
901                                                          960
AGCGCAGATCGTTGCGCTCGTTAAGGACCAAAACTAGTACTGCTGCTACTACTACGTATG
  A Q I V A L V K D Q N *
960                                                          1020
AGAACAAGGAGGAGTTCTCTGATGATGATACACACATCAAGACTTGTTTGTTGCTCTACT
```

```
1                 .              .              .              *              .    60
CCACTACATATATCTGCAACGAGCGCATCGCCAATTCACAATGCCAATTGCCAGCAACCC
61                .              .              .              .              .    120
ATCCATACTTTCAGCTGTTGATACAAAAAGAGAAGAGAGAATGGCGGAGCCAAACCCAGA
                                                    M  A  E  P  N  P  E
121               .              .              .              .              .    180
GTTGAGTGGTCTTATTACTCAAACAAAGAAGAAAAATATAGTGCCAAAGTTCACCGAAAT
  L  S  G  L  I  T  Q  T  K  K  K  N  I  V  P  K  F  T  E  I
181               .              .              .              .              .    240
CTTCCCCGTGGAGGACACGGCCTACCCTTACAGCGCCTTCATCACCTCCGTCCGGAAAGA
  F  P  V  E  D  T  A  Y  P  Y  S  A  F  I  T  S  V  R  K  E
241               .              .              .              .              .    300
AGTGATCAAATACTGCACCAACCATACAGGCATCGTCCAGCCCGTGCTGCCGCTGGAGAA
  V  I  K  Y  C  T  N  H  T  G  I  V  Q  P  V  L  P  L  E  K
301               .              .              .              .              .    360
GAATGTCCCCGAGCTCTGGTTCTACACCGAGCTCAAAACGAAGACCAGGTCCATCACGCT
  N  V  P  E  L  W  F  Y  T  E  L  K  T  K  T  R  S  I  T  L
361               .              .              .              .              .    420
CGCCATACGTATGGACAACCTCTACCTGGTCGGCTTCAGGACCCCCGGCGGGGTGTGGTG
  A  I  R  M  D  N  L  Y  L  V  G  F  R  T  P  G  G  V  W  W
421               .              .              .              .              .    480
GGAGTTCGGCAAGGACGGCGACACCCACCTCCTCGACGACAACGCCAAGTGGCTCGGCTT
  E  F  G  K  D  G  D  T  H  L  L  D  D  N  A  K  W  L  G  F
481               .              .              .              .              .    540
TGGCGGCCGGTACCAGGACCTCATCGGCAGTAAGGGCCTGGAGACCGTCACCATGGGCCG
  G  G  R  Y  Q  D  L  I  G  S  K  G  L  E  T  V  T  M  G  R
541               .              .              .              .              .    600
TGCCGAAATGACCACGGCCGTCAACTACCTGGCGAAGAAGACGACGACGACACTAGCAGA
  A  E  M  T  T  A  V  N  Y  L  A  K  K  T  T  T  T  L  A  E
601               .              .              .              .              .    660
GGCGGCGGAGGAGGAGGAGGAGCTGCTGCTGCTGCAGGCAGCGGCTGACCCCAAAGCCGA
  A  A  E  E  E  E  E  L  L  L  L  Q  A  A  A  D  P  K  A  E
661               .              .              .              .              .    720
GGAGAAGAGCAACCTGGCGAAGCTAGTGATCATGGTATGCGAGGGGCTGCGGTTCTTCAC
  E  K  S  N  L  A  K  L  V  I  M  V  C  E  G  L  R  F  F  T
721               .              .              .              .              .    780
CGTGTCCCGCAAGGTAGACGAGGGGTTCAAGAAGCCGCAAGCGGTGACCATATCGGCGCT
  V  S  R  K  V  D  E  G  F  K  K  P  Q  A  V  T  I  S  A  L
781               .              .              .              .              .    840
GGAGGGGAAGCAGGTGCAGAAATGGGACAGGATCTCGAAAGCCGTCTTCAGGTGGGCCGT
  E  G  K  Q  V  Q  K  W  D  R  I  S  K  A  V  F  R  W  A  V
841               .              .              .              .              .    900
CGACCCGACCGCTGAGATCCCCGACATGAAGGATCTTGGCATCAAAGATAAAAACGCAGC
  D  P  T  A  E  I  P  D  M  K  D  L  G  I  K  D  K  N  A  A
901               .              .              .              .              .    960
AGCGCAGATCGTTGCGCTCGTTAAGGACCAAAACTAGTACTGCTGCTACTACTACGTATG
  A  Q  I  V  A  L  V  K  D  Q  N  *
960               .              .              .              .              .    1020
AGAACAAGGAGGAGTTCTCTGATGATGATACACACATCAAGACTTGTTTGTTGCCTCTACT
```

FIG. 3.

```
       1                                                                   60
RIP2   MAEPNPELSGLITQT  KKKNIVPKFTEIFPV  EDTAYP...YSAFIT  SVRKEVIKYCTNHTG
RIP1   MAETNPELSDLMAQT  NKK.IVPKFTEIFPV  EDVNYP...YSAFIA  SVRKDVIKHCTDHKG
BR30           MAAKM    AKNVDKPLFTATFNV  QASSAD...YATFIA  GIRNKLRN..PAHFS
MAVP        APTLETIASLDL  NNPTT....YLSFIT  NIRTKVA.....DKT
RICA           IFPKQYPIINF  TTAGATVQSYTNFIR  AVRGRLTT..GADVR
SHGI   MKIIIFRVLTFFFVI  FSVNVVAKEFTLDFS  TAKTYVDSLNVIRSA 61                                                                 120
RIP2   IVQPVLP........  L.EKNVPELWFY TE  LKT....KTRS..IT  LAIRMDNLYLVGFRT
RIP1   IFQPVLP........  P.EKVPELWFY TE   LKT....RTSS..IT  LAIRMDNLYLVGFRT
BR30   HNRPVLP........  PVEPNVPPSRWFHVV  LKA....SPTSAGLT  LAIRADNIYLEGFKS
MAVP   KTEQKIS........  ....KTFTQRYSYID  LIV....SST.QKIT  LAIDMADLYVLGYSD
RICA   HDIPVLP........  NRVGLPINQRFILVE  LSN....HAE.LSVT  LALDVTNAYVVGYR.
SHGI   IGTPLQTISSGGTSL  LMIDSGTGDNLFAVD  VRGIDPEEGRFNNLR  LIVERNNLYVTGFVN 121                                                                180
RIP2   PGG.....VWWEFGK  DGDTHLLDDNAK...  ...WLGFGGRYQDLI  GSKG.L.ETVTMGRA
RIP1   PGG.....VWWEFGK  AGDTHLLGDNPR...  ...WLGFGGRYQDLI  GNKG.L.ETVTMGRA
BR30   SDG.....TWWEL..  ...TPGL IPGAT...  ...YVGFGGTYRDLL  GDTDKL.TNVALGRQ
MAVP   IANNKGRAFFFKDVT  EAVANNFFPGATGT.  NRIKLTFTGSYGDLE  K.NGGL......RK
RICA   .AGNS...AYFFHPDN  QEDAEAITHLFTDVQ  NRYTFAFGGNYDRLE  QLAGNLRENIELGNG
SHGI   RTNN....VFYRFAD  ......FSHVTFPGT  TAVTLSGDSSYTTLQ  RVAGISRTGMQINRH 181                                                                240
RIP2   EMTTAVNYLAKKTTT  TLAEAAE........  EEEELLLLQAAADPK  AEEKSNLAKLVIMVC
RIP1   EMTRAVNDLAKKKKM  ATLEEEEVQMQMQMP  EAAELAAAAAAADPQ  ADTKSKLVKLVVMVC
BR30   QLADAVTALHGRTK.  ...............  ......ADKPSGPKQ  QQAREAVTTLLLMVN
MAVP   DNPLGIFRLENSIVN  I..............  ......Y...GKAGDVK  KQAKFFLLA.IQMVS
RICA   PLEEAISAL......  ...............  ......YYYSTGGTQLP  TLARSFTIC.IQMIS
SHGI   SLTTSYLDL......  ...............  ........MSHSGTSLT  QSVARAMLRFVTVTA

300
RIP2   EGLRFFTVSRKVDEG  FKKPQAV.....TIS  ALEGKQVQKWDRISK  AVFRWAVDP.....T
RIP1   EGLRFNTVSRTVDAG  FNSQHGV.....TLT  VTQGKQVQKWDRISK  AAFEWADHP.....T
BR30   EATRFQTVSGFV.AG  LLHPKAVEKKSGKTG  NEMKAQVNGWQDLSA  ALLKTDVKPPPGKSP
MAVP   EAARFKYISDKIPSE  .KYE.EVTVDEYMTA  LE.....NNWAKLST  AVYNSKPSTTTATKC
RICA   EAARFQYIEGEMRTR  IRYNRRSAPDPSVM T  LE.....NSWGRLST  AIQESNQG...AFAS
SHGI   EALRFRQIQRGFRTT  L...DDLSGRSYVMT  AEDVDLTLNWGRLSS  VLPDYHGQ.......

301                                                                360
RIP2   AEIPDMKDLGIKDKN  AAAQ...IVALVKDQ  N*
RIP1   AVIPDMQKLGIKDKN  EAAR...IVALVKNQ  TTAAAAAATAASADN  DDDEA*
BR30   AKFAPIEKMGVRTAV  QAANTLGILLLFVEVP  GGLTVAKALELFHAS  GGK*
MAVP   QLATSPVTISPWIFK  TVEEIKLVMGLL...  .....KSS*
RICA   PIQLQRRNGSKFSVY  DVSILIPIIALMVYR  CAPPPSSQF
SHGI   ....DSVRVGRISFG  SINAILGSVALILNC  HHASRVARMASDEF  PSMCPADGRVRGITH
```

FIG. 4.

DNA ENCODING A RIBOSOME INACTIVATING PROTEIN

FIELD OF THE INVENTION

This invention relates generally to a gene which encodes a protein which inactivates ribosomal activity, and relates more specifically to a gene which encodes a such a protein found in the tissues of *Zea mays.*

BACKGROUND OF THE INVENTION

Ribosome-inactivating proteins (RIPs) comprise a large group of toxic proteins widely distributed among the plant kingdom. RIPs are most active against non-plant, eukaryotic ribosomes, although activity against prokaryotic ribosomes has been reported. See, e.g., stirpe et. al., *Biochem. J.* 262:1001-1002 (1989). RIPs inactivate ribosomes by enzymatically attacking the 60S subunit of eukaryotic ribosomes and irreversibly modifying its large ribosomal RNA (rRNA). Barbieri et. al., *Cancer Surveys* 1:129-141 (1982). This modification results from a specific RNA N-glycosidase activity that depurinates a single adenine found in a universally conserved loop of the large rRNA ($A^{4324}$), See Endo et. al., *J. Biol. Chem.* 262:8128-8130 (1987); Endo et. al. , J. Biol Chem. 262:5908-5012 (1987)) .

Given the large number of RIPs described in the literature, relatively few RIP genes have been isolated and characterized. Characterization of the maize seed pro-RIP was first reported by Soave et. al., *Cell* 27:403-410 (1981) prior to its identification as a RIP. EPO Publication No. 0 466 222 A1 discloses a RIP ("RIPi") produced in the kernels of maize in an inactive form which is activated by the cleaving of an internal peptide. The product is a two-chain active peptide moiety comprising a 16.5 kDa fragment of 169 amino acids and an 8.5 kDa fragment 107 amino acids; the dispensable region comprises 35 amino acids. The gene for the RIP1 maps to position 10 on the long arm of chromosome 8. The protein has been found only in the kernel and germinating seeds of maize. Bass et. al., *Plant Cell* 4:225-234 (1992) disclose a cDNA of the RIP1 gene. The protein coded for is highly homologous to RIP1: it has a dispensable internal region; the first fragment varies from RIP1 by only 8 amino acids; and the second fragment is identical to RIP1.

SUMMARY OF THE INVENTION

A first aspect of the present invention is isolated DNA which encodes a ribosome-inactivating protein ("RIP"). The DNA is selected from the group consisting of: (a) isolated DNA having the sequence given herein as SEQ ID NO:1: (b) isolated DNA which is at least 80 percent homologous to the isolated DNA of (a) above and encodes a RIP, and which hybridizes to an oligonucleotide probe, which probe hybridizes to isolated DNA of the sequence given herein as ID SEQ NO:3, but which probe does not hybridize to DNA of the sequence given herein as ID SEQ NO:5; and (c) isolated DNAs differing from the isolated DNAs of (a) and (b) above in nucleotide sequence due to the degeneracy of the genetic code, and which encode a RIP. The DNA preferably encodes a Zea RIP.

A second aspect of the invention is a 35 recombinant DNA comprising vector DNA and a DNA as described in (a)-(c) above. Preferably, the recombinant DNA resides in a host cell suitable for transcription and translation.

A third aspect of the invention is an oligonucleotide probe which selectively hybridizes to isolated DNA having the sequence given herein as SEQ ID NO:3, but which is not capable of hybridizing to isolated DNA having the sequence given herein as SEQ ID NO:5.

A fourth aspect of the invention is a RIP encoded for by DNA as defined in (a)-(c) above. A preferred use for the protein is in an agricultural agent which comprises the RIP and a suitable agricultural carrier.

A fifth aspect of the invention is a transgenic plant comprising a promoter operable in the cells of the plant and DNA as described above which is operatively associated with the promoter.

BRIEF DESCRIPTION OF THE DRAWINGS

FIG. 1 is a restriction map of plasmid pRIP2-B6. The restriction map of an internal BamHI fragment from a lambdaRIP2 subclone was determined by electrophoretic analysis of digested DNA. The sites shown and their positions (in kb) relative to the first BamHI site are BamHI (B, O, 6.26) , EcoRI (E, 1.8, 6.26) , HincII (Hc, 0.63, 3.8, 4.1, 5.15, 6.0) , KpnI (K, 3.73) , Sinai (Sin, 2.79) , SstI (Ss, 0.52, 0.87, 3.58) , XbaI (X, 5.75) . Of those tested only XhoI is not present within the subclone. Plasmid vector sites from the polylinker of pBluescript (KS/+) shown for orientation are KpnI (vK, −0.06) and SstI (Vs, 6.30). The coding region predicted from sequence analysis is shown by an open box with the orientation of the transcript (5', 3') indicated. Also shown are the positions of the predicted transcriptional initiation site (bent arrow), and the location of the oligonucleotide used for primer extension reactions (*). The positions of subclones used for synthetic RNA production (PS), or probes (5'800, RMA89) are shown.

FIG. 2 is a Southern blot analysis of the Maize RIP2 gene. DNA from pRIP2-B6 (Copy #) was digested with EcoRI. DNA from genomic clone lambdaRIP2 (lambdaRIP2) or maize DNA from inbred W64A (Maize) was digested with EcoRI (E), BamHI (B), or HindIII (H). The DNAs on the filter were hybridized at Tm-32° C. with a $^{32}P$-labeled RIP1 cDNA (ZmcRIPO-3). Copy number reconstructions were based on a maize haploid genome size of 5.3 pg. Molecular weight markers (M) are indicated at right in kb. Bands from maize DNA corresponding to those from lambdaRIP2 are marked with circles (o) .

FIG. 3 is a nucleotide and deduced amino acid sequence of a maize RIP2 genomic clone. The sequence corresponding to the coding region and nearby flanking regions is shown. The deduced amino acid sequence of RIP2 is indicated below the DNA sequence, and the start and stop codons are printed in bold type. A putative TATA box beginning at position 5 is double underlined. An asterisk (*) marks the putative transcription start site.

FIG. 4 is a comparison of primary structures of RIPs. RIP2, RIP1, BR30, and MAVP denote amino acid sequences of plant type 1 RIPs derived from the maize pRIP2-B6 genomic clone; the maize seed proRIP cDNA, ZmcRIP-9; the barley seed RIP cDNA, BR30; and the Mirabilis antiviral protein cDNA (MAP), respectively. RICA and SHGI denote amino acid sequences derived from the cDNA for the A-chain of castor bean ricin (a type 2 RIP), and the genomic clone for the type 1 shiga toxin (a prokaryotic RIP) from *Shigella dysenteriae.* Sequences were multiply aligned by introduction of gaps ( ... ) to maximize similarity. The ricin A-chain and MAP start at residues that reflect cotranslational processing points. Similarly, COOH-terminal residue shown for the ricin A--chains (F) represents that found in the native protein. Bold type indicates an identity among at least 4 of the 5 plant RIP sequences at a given position and open circles indicate invariant residues among plant RIPs. Asterisks (*) denote stop codons and numbers identify positions within the alignment. The central portion of pro-RIP (RIP1) that is absent from the mature RIP is underlined.

FIG. 5 shows the presence of RIP2 RNA in various plant parts. RNA gel blot of equal amounts of total RNA (12 $\mu$g, except kernel [5 $\mu$g] and synthetic RNA [10ng]) from various sources was incubated with the gene-specific radiolabeled RIP2 fragment, RMA89 (specific activity $1\times10^9$ cpm/$\mu$g). RNA was purified from mature tassel that was shedding pollen (1), immature preemerged tassel (2) , mature silk (3) , husk (4) , greenhouse-grown leaf (5), field-grown leaf (6), seedling shoot (7), prop roots (8), BMS suspension culture (9), endosperm suspension culture ( 10 ) , opaque-2 20 DAP kernel ( 14 ) , or normal 20 DAP kernel (15). Synthetic RNA was made from a cloned RIP1 cDNA (13) or a cloned RIP2 genomic DNA (12). The hybridization was carried out at Tm-88° C. and the filter was exposed for 430 h at −80° C. with an intensifying screen. The positions of RIP2 RNA (arrow), and the large (1R−) and small (sR−) ribosomal RNA are indicated at left.

FIG. 6 shows the presence of RIP2 and RIP1 RNA during opaque-2 mutant kernel development by an RNA gel blot of equal amounts of total RNA (10 $\mu$g) from developing opaque-2 kernels. The age of the ear at the time of harvest is indicated at the top. A HindIII-SstI fragment from the coding region of a RIP1 eDNA was radiolabeled to a specific activity of $2\times10^9$ cpm/$\mu$g and incubated with the RNA at $T_m-32°$ C. (RIP). RIP1(−1) and RIP2 RNA (−2) bands are indicated at right. The lower panel is a duplicate gel visualized by acridine orange staining.

FIG. 7 shows the optimization of a primer extension assay. Primer extension products were purified, fractionated, and visualized by autoradiography. Reactions consisted of $5\times10^3$ cpm end-labeled oligonucleotide plus 0.5 ng synthetic RNA (RIP2, RIP1), 10 $\mu$g tRNA (tRNA), 5 $\mu$g BMV RNA (BMV RNA), or 30 $\mu$g total RNA from maize (20 DAP kernel, Endosperm s.c., or BMS s.c.). Additional reaction specifications are described in Example 9. Experimental variables are listed. Lanes not specifying temperature or time consisted of 45° C. 60 min reverse transcription reactions. Molecular weight markers (M) are indicated at right in nt.

FIG. 8 shows the results of a primer extension analysis of maize RNAs. Primer extension reactions were carried out and visualized as described in FIG. 4.7. Reverse transcription reaction conditions employed for all samples were 37° C. 60 min. Headings above the lanes indicate the sources of RNA. Molecular weight markers (M) are indicated at right in nt.

FIG. 9 shows the results of an aniline cleavage assay for RIP activity of synthetic RIP2 RNA translation products. RNA isolated from rabbit reticulocyte translation extracts (40 $\mu$L reactions per treatment) was separated on a 4.5% denaturing gel and visualized by ethidium bromide staining. Translation reactions received BMV RNA (BMV), gelonin (GLN), RIP2 synthetic RNA-sense strand (R2+), or RIP2 synthetic RNA-antisense strand (R2−). Aliquots of purified RNA were prepared for electrophoresis (lanes with odd #s) or treated with aniline (lanes with even #s) before electrophoresis. The arrow indicates the aniline cleavage product diagnostic for RIP-modified RNAs.

DETAILED DESCRIPTION OF THE INVENTION

As noted above, ribosome-inactivating proteins are proteins which inactivate or severely reduce the activity of ribosomes, in particular nonplant eukaryotic ribosomes, although inactivation of prokaryotes and viruses has been observed. This activity makes these proteins useful in a variety of ways. They can be used to fight pests in crops, either as an applied pesticide formulation or by incorporation into the genome of the plant. They also have utility as, among others, immunotoxins and anti-viral agents. Further, they are useful in vitro to arrest protein translation from RNA in biochemical assays where a precise termination of the reaction is desired.

1. DNA Encoding Ribosomal Inactivating Proteins.

In general, and as explained in greater detail below, DNA encoding RIPs of the invention includes DNA which is 80 percent homologous or more with DNA having the sequence given herein as SEQ ID NO:1. With respect to the protein, DNA encoding this RIP encode a protein which, in amino acid content, is about 80 percent homologous or more, or preferably about 85% homologous or more, with the protein having the amino acid sequence given herein as SEQ ID NO:2. Determinations of homology are made with the two sequences (nucleic acid or amino acid) aligned for maximum 15 matching. Gaps in either of the two sequences being matched are allowed in maximizing matching. Gaps lengths of 10 or less are preferred, gap lengths of 5 or less are more preferred, and gap lengths of 2 or less still more preferred.

The DNA can be recovered from within the cells of it natural host, or it can be synthesized directly. Exemplary are direct syntheses are chemical syntheses, which include manual procedures, such as the phosphodiester or phosphotriester methods, see Caruthers, in *Methodology of DNA and RNA* (Weisman ed. 1983), and automated procedures. Also, the DNA may be constructed by standard techniques of annealing and ligating fragments or by other methods. Also exemplary are cloning procedures discussed in section 3 below.

The present invention also includes DNA sequences which hybridize to oligonucleotide probes which hybridize to DNA defined by SEQ ID NO:3 but do not hybridize to DNA defined by SEQ ID NO:5 and which code on expression for a RIP. Conditions under which such sequences will so hybridize can be determined in a routine manner. For example, hybridization of such sequences may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA having the sequence given as SEQ ID NO:1 herein in a standard in situ or filter hybridization assay. See J. Sambrook et. al., Molecular Cloning, A Laboratory Manual (2d Ed. 1989)(Cold Spring Harbor Laboratory)). In general, such sequences will be at least 80 percent homologous, 85 percent homologous, 90 percent homologous, or even 95 percent homologous or more with the sequence given herein as SEQ ID NO:1. Determinations of homology are made with the two sequences aligned for maximum matching. Gaps in either of the two sequences being matched are allowed in maximizing matching. Gap lengths of 10 or less are preferred, gap lengths of 5 or less are more preferred, and gap lengths of 2 or less still more preferred. Those skilled in this art will appreciate that a DNA sequence of this sort will encode a RIP which has portions of its amino acid sequence which are equivalent to amino acid sequences obtained directly from nature and will exhibit essentially biological activity.

Promoters employed in carrying out the present invention may be active in numerous different plant tissues. SEQ ID NO:1 includes therein a promoter region for the RIP gene. This promoter region can be DNA which controls the expression of the RIP gene and which is 40, 50, 60, or even 70 percent homologous with the promoter region of SEQ ID NO:1. In addition, several plant and viral genes are actively expressed in multiple tissues. Exemplary genes encode the B-subunit of the mitochondrial ATPase complex, B-tubulin, actin, acetohydroxyacid synthase, and the 35S RNA of cauliflower mosaic virus.

2. Ribosomal Inactivating Proteins.

RIPs encompassed by the present invention include proteins having the amino acid sequence given as ID SEQ NO:2 and proteins homologous to, and having essentially the same biological properties as, the protein disclosed herein as SEQ ID NO:2. This definition is intended to encompass natural allelic variations in the protein, although at least one embodiment has been found to be nonallelic. It will be appreciated that the amino acid sequence need not be identical to that of SEQ ID NO:2; for the purposes of this invention, the amino acid sequence may be at least 80 percent, 85 percent, 90 percent, or even 95 percent homologous or more with the protein of SEQ ID NO:2 to retain its biological activity. General categories of potentially equivalent amino acids include, but are not limited to: glutamic acid and aspartic acid; lysine, arginine, and histidine; alanine, valine, leucine, and isoleucine; asparagine and glutamine; threonine and serine; phenylalanine, tyrosine and tryptophan; and glycine and alanine. These proteins can be produced by recombinant methods as described below, by synthesis of the RIP from its constituent amino acids, or other methods.

The RIP of the present invention can be produced by standard techniques for isolating proteins from biological systems, such as salt precipitation, column chromatography, immunoaffinity techniques, electrophoresis, recrystallization, centrifugation, and the like. In addition, the RIP can be raised by recombinant techniques, wherein cDNA clones for the DNA sequence encoding the RIP of the present invention are produced, isolated, proliferated, and transferred to a suitable host cell, such as $E.$ $coli.$ In the host cell, the DNA sequence produces the RIP in far greater abundance than that seen in its natural environment.

3. Genetic Engineering of Plants

DNA constructs, or "transcription cassettes," of the present invention include, 5'-3' in the direction of transcription, a promoter as discussed above and, optionally, a termination sequence including stop signal for RNA polymerase and a polyadenylation signal for polyadenylase (e.g., the nos terminator). All of these regulatory regions should be capable of operating in the cells of the tissue to be transformed. The 3' termination region may be derived from the same gene as the transcriptional initiation region or may be derived from a different gene.

The transcription cassette may be provided in a DNA construct which also has at least one replication system. For convenience, it is common to have a replication system functional in $Escherichia$ $coli,$ such as ColE1, pSC101, pACYC184, or the like. In this manner, at each stage after each manipulation, the resulting construct may be cloned, sequenced, and the correctness of the manipulation determined. In addition, or in place of the $E.$ $coli$ replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complimentation, by imparting prototrophy to an auxotrophic host; or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are luciferase, providing visible light production, NPTII, providing kanamycin resistance or G418 resistance, HPT, providing hygromycin resistance, phosphinothricin acetyl transferase encoded by the bar gene of streptomyces provides resistance to bialophos and BASTA, and the mutated aroA gene, providing glyphosate resistance.

The various fragments comprising the various constructs, transcription cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Maniatis et. al., supra.

Vectors which may be used to transform plant tissue with DNA constructs of the present invention include both Agrobacterium vectors and ballistic vectors, as well as vectors suitable for DNA-mediated transformation.

Methods of making recombinant ribosome-inactivating plants of the invention, in general, involve providing a plant cell capable of regeneration (the plant cell typically residing in a tissue capable of regeneration). The plant cell is then transformed with a DNA construct comprising a transcription cassette of the present invention (as described herein) and a recombinant ribosome-inactivating plant regenerated from the transformed plant cell. As explained below, the transforming step is carried out by bombarding the plant cell with microparticles carrying the transcription cassette, by infecting the cell with an $Agrobacterium$ $tumefaciens$ containing a Ti plasmid carrying the transcription cassette, electroporation of immature embryos, or any other technique suitable for the production of a transgenic plant.

Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et. al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et. al., U.S. Pat. No. 5,015,580. When using ballistic transformation procedures, the transcription cassette may be incorporated into a plasmid capable of replicating in the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the transcription cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be shelfed to give homozygous second generation (or T2) transformed plants, and the T2 plants further propagated through classical breeding techniques. A dominant selectable marker (such as npt II) can be associated with the transcription cassette to assist in breeding.

Plants which may be transformed by the techniques described above include species of the following genera (with exemplary species in parentheses): *Zea mays* (maize); *Gossypium hirstium*(cotton) ; *Nicotinia tabacura* (tobacco); *Solanum tuberosum* (potato); *Glycine max* (soybean); Arachis *hypogaea* (peanut); *Dendranthema* spp. (chrysanthemum); *Brassica napus* (oil seed rape); *Sorghum bicolor* (sorghum); *Triticum aestivum* (wheat); *Oryza sativa* (rice) and *Lycopersicon esculentum* (tomato). Particular pathogens which can be resisted by the present invention include: *Phytophthora parasitica* var. *nicotinae* (root-infecting blank shank) , *Alternaria alternata* (foliar-infecting brownspot); *Fusarium oxysporum; Fusarium moniliforme; Rhizoctonia solani; Aspergillus flavus; Diabrotic virgifera* (Western corn rootworm); *Callosobruchus maculatus* (cowpea seed weevil); *Anthonomus grandis* (cotton bollweevil ); and *Meloidogyne incognita* (root-knot nematode) .

The present invention is explained in greater detail in the following non-limiting examples. These examples are provided so that the invention can be more completely understood and are not to be construed as restrictive of the invention. Amino acid sequences disclosed herein are presented in the amino to carboxyl direction, from left to right. The amino and carboxyl groups are not presented in the sequence. Nucleotide sequences are presented herein by single strand only, in the 5' to 3' direction, from left to right.

In the Examples, "kb" means kilobases, "$2_6$" means light absorption at 260 nanometers, "$\mu$g" means micrograms, "Mi" means milliliters, "Mm" means millimoles, "°C", means degrees Centigrade, "L" means liters, "bp" means base pairs, "nt" means nucleotide, "h" means hours, "ng" means nanograms, "CDNA" means carrier DNA, and "rain" means minutes. In the Figures showing amino acid sequences, "A" means adenine, "T" means thymine, "G" means guanine, and "C" means cytosine". In the Figures showing protein sequences, "A" means alanine, "M" means methionine, "E" means glutamic acid, "P" means proline, "N" means asparagine, "L" means leucine, "S" means serine, "G" means glycine, "I" means isoleucine, "T" means threonine, "Q" means glutamine, "K" means lysine, "V" means valine, "F" means phenylalanine, "D" means aspartic acid, "Y" means tyrosine, "R" means arginine, "C" means cysteine, "H" means histidine, and "W" means tryptophan.

EXAMPLE 1

Collection and Care of Plant Materials

Maize was grown and harvested as described by Bass et. al., (1992) and included 1992 field- or greenhouse-grown plants (Raleigh, NC). Tissues were harvested and immediately frozen in liquid nitrogen. Field-grown roots and prop roots were briefly rinsed with water to remove soil before freezing. Black Mexican sweet corn (BMS) suspension culture was obtained from Ciba-Geigy, Corp. Research Triangle Park, NC, and maintained as described in Green, *Hort. Sci.* 12:131-134 (1977). Endosperm suspension culture was initiated from a hybrid maize line available from North Carolina State University, Raleigh, North Carolina, and was maintained as described in Shannon, Maize endosperm cultures in *Maize for Biological Research* 397–400 (W. F.

Sheridan ed., Grand Forks, ND: Univ. North Dakota Press, 1982). Cultured cells were collected by filtration through cheesecloth prior to freezing in liquid nitrogen.

EXAMPLE 2

Molecular Cloning of RIP2

A maize (inbred W64A) DNA library in lambdagem11 (Promega, Madison WI) was constructed and made available by G. J. Wadsworth and J. G. Scandalios (described in Wadsworth et. al. *Anal. Biochem.* 172:279-283 (1989). The library, which comprises leaf DNA partially-digested by SauA I, was screened by hybridization at Tm-30° C. with a RIP1 cDNA clone (pZmcRIP-3, Bass et. al., supra) radiolabeled with $^{32}$P-dCTP. A class of cross-hybridizing clones with restriction enzyme patterns similar but not identical to that of the RIP1 gene was repeatedly isolated.

A 6.3 kb Bam HI restriction fragment from a representative member of these clones (lambdaRIP2C6) was subcloned into the Bam HI site of Pbluescript to produce the plasmid designated pRIP2-B6. Suitable subclones of pRIP2-B6 were sequenced by the dideoxynucleotide chain termination method (Sanger et. al., *Proc. Natl. Acad. Sci. USA.* 74:5463-5467 (1977) using the Sequenase TM enzyme. Sequence analysis was performed with the SeqEd and fragment assembly programs of the Genetics Computer Group software package (GCG, Madison, WI). Subclones of pRIP2-B6 were also used for probe preparation and RNA synthesis.

The restriction enzyme map of pRIP2-B6 is presented schematically in FIG. 1. The position of an open reading frame derived from the DNA sequence is indicated in FIG. 1 as an open box. The restriction sites indicated above the line were determined by electrophoretic analysis of restriction fragments.

EXAMPLE 3

Genomic Southern Blot Analysis of Maize RIPs

To identify the maize DNA fragments that corresponded to the lambdaRiP2 clone produced in Example 2, a genomic Southern blot analysis was performed. DNA was isolated from bacteriophage lambdaRiP2 according to the method of Maniatis et. al., supra. For DNA from W64A ear shoot material, the method of Zimmer et. al., A simple method for the isolation of high molecular weight DNA from individual maize seedlings and tissues, in *Maize for Biological Research* 164–168 (W. F. Sheridan ed., Grand Forks, ND: Univ. North Dakota Press (1982), was scaled up and followed through the step for proteinase K treatment. DNA was purified from the resulting solution by centrifugation in CsCl as described by Maniatis et. al. supra, and quantified by UV absorbance spectroscopy. DNAs were digested with restriction enzymes, quantified by UV spectroscopy (1.0 $A_{260}$=50 μg/mL), fractionated on a 1% (weight:volume) agarose/TBE gel (TBE is 89 mM tris[-hydroxymethyl] aminomethane, 89 mM boric acid, 2 mM EDTA-NaOH; pH=8), and transferred to a nylon membrane (GeneScreen, NEN) by the capillary blotting method of Southern, *J. Mol. Biol.* 98:503-517 (1977). All filter hybridization steps were kept at $T_m$−30° C. The methods of probe preparation hybridization and autoradiography were performed as previously described in Bass et. al., supra. Hybridization stringency determinations were based on the formulas described by Casey et. al., *Nucleic Acids Res.* 4:1539-1549 (1977) and Wetmur et. al., *J. Mol. Biol.* 31:349-370 (1968). The formula used was $T_m$=81.5° C.+16.6×log[salt]+0.41% (%G+C)−650L. In the formula, L is the average length of the probe in nucleotides.

Figure 2:
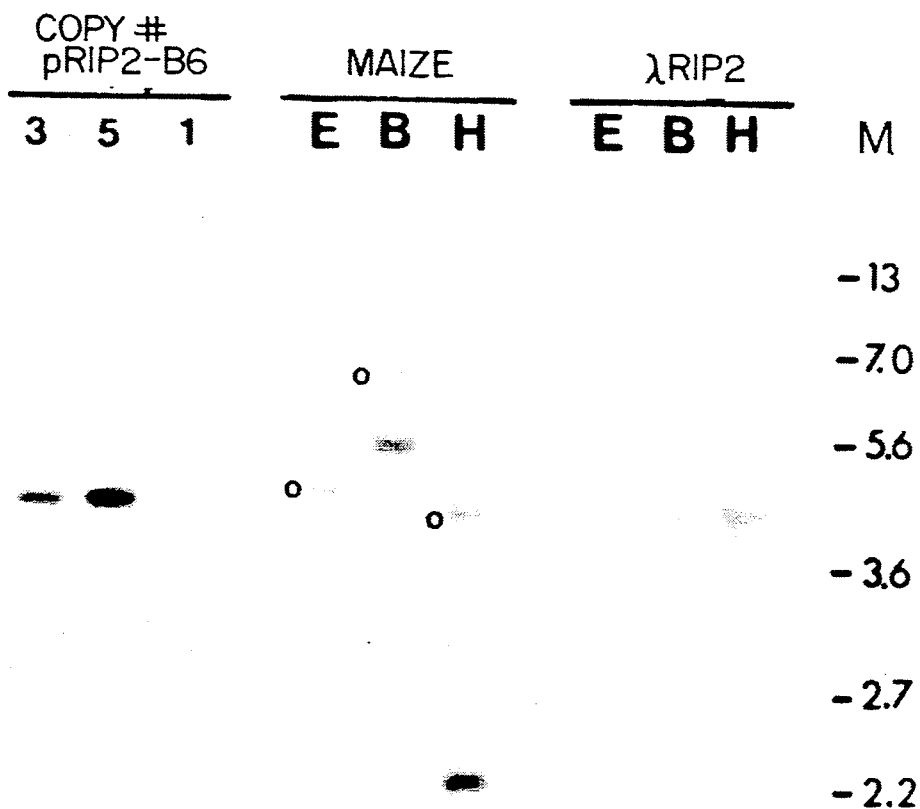

The results of the analysis are shown in FIG. 2. In order to observe all RIP-like sequences, a radiolabeled maize RIP1 cDNA clone (ZmcRIP-3, Bass et. al., supra), was hybridized at moderate stringencies to maize DNA digested with EcoRI, BamHI, or HindIII (lanes E, B, or H, respectively). The blot also contained lanes with lambdaRIP2 DNA (lambdaRIP2 Lanes) digested with the same enzymes to allow correlation of fragments from genomic DNA with restriction fragments from the clone. Only one band per lane was detected from lambdaRIP2. These were determined to be 4.3 kb (lanes E), 6.3 kb (lanes B), and 4.0 kb (lanes H). A corresponding set of bands from maize DNA (Maize) was observed and was indicated with circles (o).

The 6.3 kb BamHI band represents the fragment subcloned as plasmid pRIP2-B6 (FIG. 1). This band also contained the 4.3 kb EcoRI fragment. These results indicated that the lambdaRIP2 DNA had not undergone any major rearrangement during cloning.

In addition to the RIP2 bands, maize contained bands determined to be approximately 18 kb and 30 kb in the EcoRI-digested DNA (Maize section), 5.5 kb in the BamHI digested DNA, and 2.15 kb in the HindIII digested DNA. These fragments were presumed to harbor the RIP1 gene. A copy number reconstruction (copy #pRIP2-B6) was made with EcoRI-digested pRIP2-B6. By comparison with the maize genomic DNA, it was determined that the maize RIP2 sequences (bands marked by o) were present at approximately 1 copy per haploid genome. Because the probe had been made from a full length RIP1 cDNA, the homologous maize bands containing RIP1 showed a stronger hybridization signal than did those containing RIP2. This difference most likely resulted from mismatch of the heterologous RIP1:RIP2 hybrids, especially for the 120 nt 3 min of the RIP1 cDNA coding region. For this reason, an accurate copy number reconstruction can be made for the RIP2 gene but the comparison can not be extended to the RIP1 genes.

EXAMPLE 4

Chromosomal Localization of the RIP2 RFLP Locus

An 800 bp SmaI-SstI restriction fragment from pRIP2-B6 was used as a probe to determine the chromosomal position of RIP2 (FIG. 1, 5'800). The RFLP blots contained maize DNA from two sets of recombinant inbred lines from a permanent mapping population (Burr et. al., *Trends Genet.* 7:55–60 (1991)). The probe detected only one restriction fragment that differed in size from one parental line to another. This RFLP was scored and mapped to chromosome 7L between the RFLP loci BNL8.21A and BNL7.61.

EXAMPLE 5

DNA Sequence Determination of a RIP2 Genomic Clone

The sequence of a portion of pRIP2-B6 that showed cross-hybridization with RIP1 eDNA was determined as described in Example 2. This sequence is shown along with the deduced amino acid sequence in FIG. 3. The DNA sequence allowed prediction of an open reading frame of 278 amino acids. No introns were observed, although a corresponding cDNA was not isolated to confirm this. The presumed start (ATG) and stop (TAG) codons are indicated by bold letters. The proportion (68%) of codons specifying C or G in the third position was consistent with the codon usage of cloned maize nuclear genes (Campbell et. al., *Plant Physiol.* 92:1-11 (1990)). The putative peptide did not show features of an NH2-terminal signal peptide for synthesis on the ER (Von Heihn, *Nucleic Acids Res.* 14:4683-4690 (1990)). A sequence upstream of the start codon resembling a TATA box is underlined. In comparison with the RIP1 cDNA (ZmcRIP-9), the DNA identity within the coding region is 83%. This level of similarity drops to 60% in the 100 nt span 5' of the coding region and to 54% in the 130 nt span 3' of the coding region.

COMPARATIVE EXAMPLE A

The amino acid sequence deduced from RIP2 was compared with those of several other RIPs. The sequence alignment is presented in FIG. 4. The RIP2 sequence (RIP2) was aligned with sequences of the maize pro-RIP, ZmcRIP-9 (RIP1); RIP30 (RP30), a type 1 RIP from barley seed; the A-chain of ricin (RICA), a type 2 RIP from castor bean; the Mirabilis antiviral protein or MAp (MAVP), a type 1 RIP from the roots of Mirabilis, and the type I shiga toxin (SHGI), a microbial RIP from *Shigella dysenteriae*. The NH2-terminal residues shown for ricin A--chain and MAP and the COOH-terminal residue shown for the ricin A--chain represent the terminal amino acids found in the native protein (Halling et. al. *Nucleic Acids Res.* 13:8019-8033 (1985); Habuka et. al., *J. Biol. Chem.* 264:6629-6637 (1989)). The 21 COOH-terminal residues of the shiga toxin did not align with any plant RIPs and are not shown.

RIPs commonly exhibit a low overall homology with each other, but have strict conservation of some residues (Ready et. al., Proteins 3:53-59 (1988)). A recent display generated with the GCG pileup program for multiple sequence alignment showed 10 positions of invariant residues among the 15 plant RIPs compared (data not shown). The positions of these 10 residues are identified here as open circles (o) above the RIP2 sequence. Five of these invariant residues, Y-119, Y-166, E-241, R-244, and W-295 have been determined to reside in the presumed active site cleft of the ricin A-chain as determined by X-ray crystallography and mutagenesis studies (Montfort et. al. *J. Biol. Chem.* 262:5398-5403 (1987); Ready et. al., Proteins 10:270-278 (1991); Frankel et. al., *Mol. Cell. Biol.* 9:415-420 (1989); Katzin et. al., *Proteins* 10:251-259 (1991)). Small blocks of homology such as PVLP at 64-67, TLAI at 105-108, and FGG at 157-159 were revealed by highlighting residues identical in 4 of the 5 plant RIPs (FIG. 4), yet the basis for their conservation is unknown.

The maize pro-RIP (line RIP1) undergoes a proteolytic activation that results in removal of amino acids from both termini as well as an internal region (Walsh et. al., *J. Biol. Chem.* 266:23422-23427 (1991)). The boundaries of the internal region removed were deduced from direct sequencing of an active RIP preparation, and the region removed is underlined in FIG. 4 (positions 194-220). Interestingly, RIP2 also contained extra amino acids in this region (194-220).

EXAMPLE 7

Expression of the RIP2 gene

To analyze expression of the RIP2 gene, it was first necessary to identify probes that would distinguish between RIP1 and RIP2 transcripts. A gene-specific probe was isolated from an internal 89 bp RmaI restriction fragment of pRIP2-B6 that had identity with only 65% of the nucleotides in the corresponding region of RIP1. The position of this RmaI fragment within pRIP2-B6 is shown in FIG. 1 (RMA89). $T_m - 8°$ C. was chosen as the hybridization stringency for probing RNA prepared from various plant parts with radiolabeled RMA89 because at a hybridization stringency of $T_m - 8°$ C., sequences with greater than 10% mismatch should not anneal (Bonner et. al., *J. Mol. Biol.* 81:123 (1973)).

For the procedure, RNA was isolated from developing kernels as described in Langridge et. al., *Planta* 156:166-170 (1982). RNA from non-kernel tissues was isolated by the phenol/SDS method for plant RNA preparation (Ausubel et. al., *Current Protocols in Molecular Biology* (New York: Greene Publishing Associates, Wiley-Interscience 1992) modified by the addition of polyvinyl-pyrrolidone and polyvinyl-polypyrrolidone (PVP-360 and PVPP, Sigma Chem. Co., St. Louis, MO) to 1% (weight:volume) each in the initial grinding buffer, and the subsequent addition of a LiCl precipitation step (4 M LiCl, 4° C., 12 h) following resolubilization of the pellet collected after precipitation by isopropyl alcohol. The RNA was dissolved in 0.1 mL H2O per gram starting tissue, and was then quantified by absorbance spectroscopy using the equation 40 μg/mL = 1.0 $A_{260}$ Unit.

Figure 5:
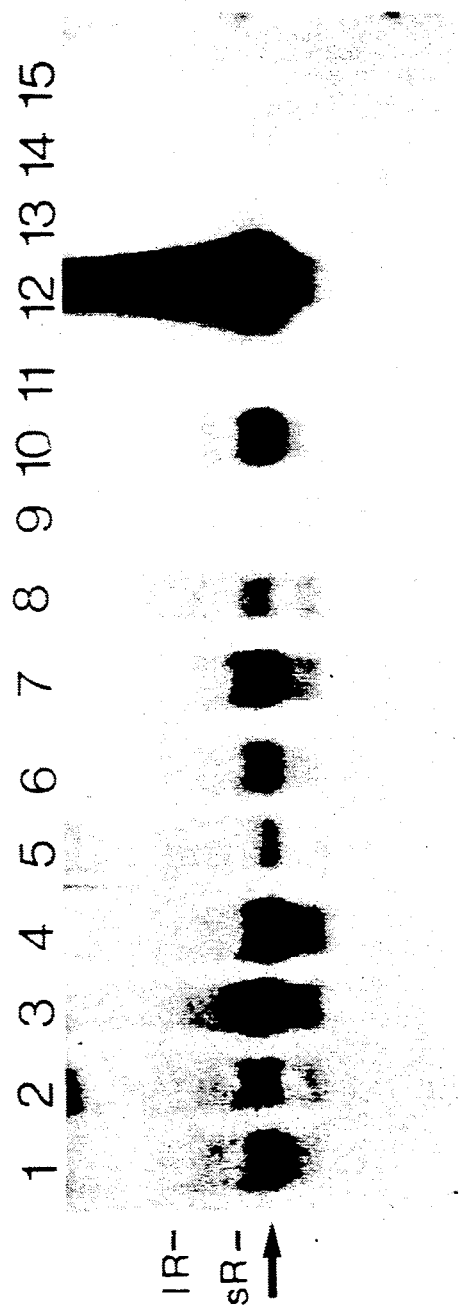

The results of the RNA gel analysis are shown in FIG. 5. A strong signal (arrow) was observed for RNA prepared from tassel (1), silk (3), husk (4), seedling shoot (7), and endosperm suspension culture (10). This signal was not due to RIP1 RNA and likely represented transcripts from the RIP2 gene. This assertion is based on the comparison of internal controls which contained either 10 ng of synthetic RIP2 RNA (12) or 10 ng of synthetic RIP1 RNA (13). These RNAs were sense-strand RNAs produced in vitro. A template for synthetic RNA was made from a subclone of pRIP2-B6. An 864 bp PVU II, Sca I restriction fragment was ligated into the Sma I site of pBluescript. The plasmid was designated pPST7 (5' end adjacent to the T7 promotor in the vector). The plasmid pZmcRIP-3 used for preparation of RNA for RIP1 contained a full-length maize RIP1 cDNA (5' end adjacent to the T3 promoter in Bluescript) and has been described previously by Bass et al., supra (1992). For RNA production from either strand of the cloned RIP2 gene, template plasmids were linearized by restriction enzyme digestion at a single site and transcribed in vitro with T7 or T3 RNA polymerases according to standard procedures. Thus, at the stringency used, the RMA89 probe did not show any detectable hybridization with RIP1 RNA.

In addition to the RIP2 RNA bands, a weaker band (arrow) of the same size was detected in RNA from immature tassel (2), leaf (5.6), and prop root (8). No bands were detected in RNA from a Black Mexican Sweet corn (BMS) suspension culture (9), opaque-2 mutant (14) or normal (15) kernels harvested at 20 DAP. In three lanes an additional band was observed just above the RIP2 RNA band (2, 6, 8). These larger bands may have resulted from the presence of the abundant small rRNA (position indicated as -sR) which appeared to displace the background signal within a lane. Such displacement toward the bottom of the gel would result in a compact band. RNA from prop root (8) and immature tassel showed a faint band below the RIP2 RNA signal. Neither the source nor the significance of this band is known. The data shown indicates that most non-kernel plant parts contained RIP2 RNA.

Additionally, the reason for background signal in some but not all lanes is not known. One possibility could be that the background reflects the variation in the amount of organellar or microbrial RNA present that may be cross hybridizing with trace amounts of radiolabeled *E. coli* fragments.

The difference in migration of the RIP2 RNA band in the silk RNA (3) coincided with a similar distortion of the entire RNA sample as determined by acridine orange staining of a duplicate gel prepared from the same glyoxalation reaction (data not shown). These distortions were assumed to result from contaminating molecules, possibly polysaccharides, that copurified with the RNA.

EXAMPLE 8

RNMA Accumulation Patterns of RIP2 and RIP1 in Developing opaque-2 Kernels

To observe both RIP1 and RIP2 RNA in a single gel blot, an internal radiolabeled RIP1 cDNA fragment was hybridized to kernel RNA at a moderate stringency ($T_m - 32°$ C.). RNA from developing opaque-2 kernels was chosen because it had been determined previously that a low level of RIP1 RNA was present at specific developmental stages (Bass et. al., supra). The lowered stringency and use of an internal restriction fragment as a probe also guaranteed cross-hybridization with any RIP2 that may also be present.

Figure 6:
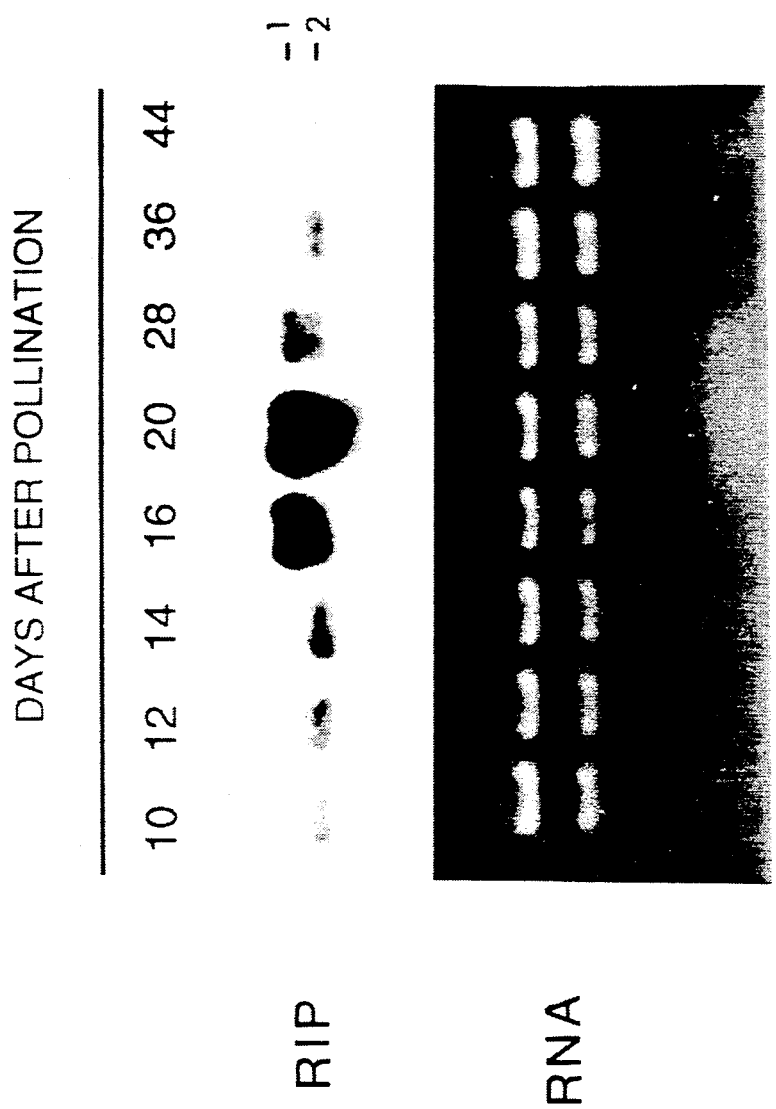

FIG. 6 shows that by this approach, both RIP1 and RIP2 RNA were detected. The upper band (−1) was approximately 1200 nt and determined to be from the RIP1 gene because of its characteristic developmental pattern of being most abundant at 16 and 20 DAP. The lower band of approximately 950 nt (−2) was considered to be RIP2 RNA and was detected in RNA samples from 10, 12, 14, 28, 36 and 44 DAP. Whether or not RIP2 RNA was present at 16 and 20 DAP could not be determined because its predicted position would be obscured by the signal from RIP1 RNA. The possibility that the band presumed to be RIP2 RNA represented neither RIP1 nor RIP2, but a third cross-hybridizing species has not been ruled out. However, the detection of only two RFLP loci with a RIP1 cDNA probe is consistent with the interpretation that the two bands represent the two maize RIPs.

EXAMPLE 9

Primer Extension Analysis of RIP1 and RIP2 Genes

To identify the site of transcriptional initiation of the RIP2 gene, and to better discriminate between the RIP1 and RIP2 transcripts, a primer extension analysis was performed as described in Asubel et. al., supra, except as otherwise noted. The synthetic DNA oligonucleotide (5'GGTGCAGTGTTTGATCAC3') and Hae III restriction fragments from the plasmid pBluescript were end-labeled with $^{32}$P using T4 polynucleotide kinase according to manufacturer's instructions (New England Biolabs, Inc., Beverly, MA). RNA for use as internal controls in gel blots and primer extension assays was synthesized *in vitro* with the enzyme T3 RNA polymerase as instructed by the manufacturer (MEGAscript TM kit, Ambion, Inc., Austin, TX). The plasmid templates used were BamHI-digested pPST3 for synthesis of RIP2 RNA and XbaI-digested pZmcRIP-3 for synthesis of RIP1 RNA.

Following transcription, the DNA was removed by treatment with DNAseI, and the RNA was phase extracted with phenol/chloroform (1:1), ethanol precipitated, and redissolved in $H_2O$. RNA quality was determined by gel fractionation and ethidium bromide staining to confirm the presence of a single species of RNA (data not shown), and quantified by UV absorbance spectroscopy.

Figure 7:
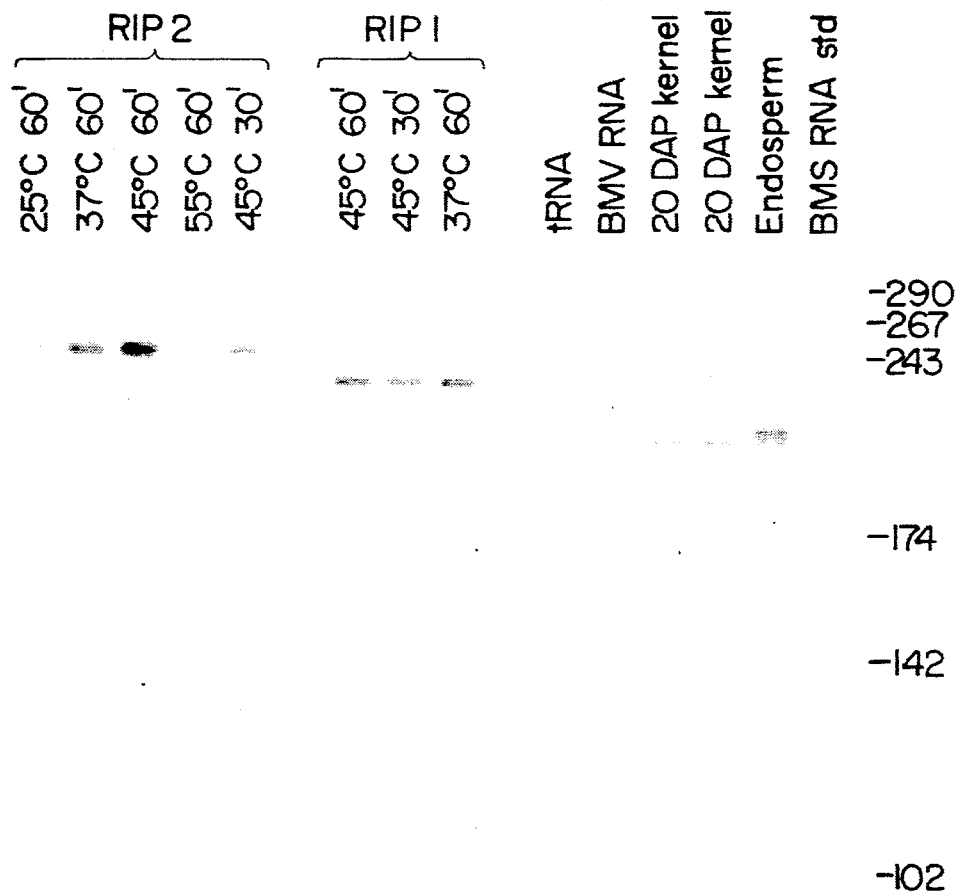
Figure 8:
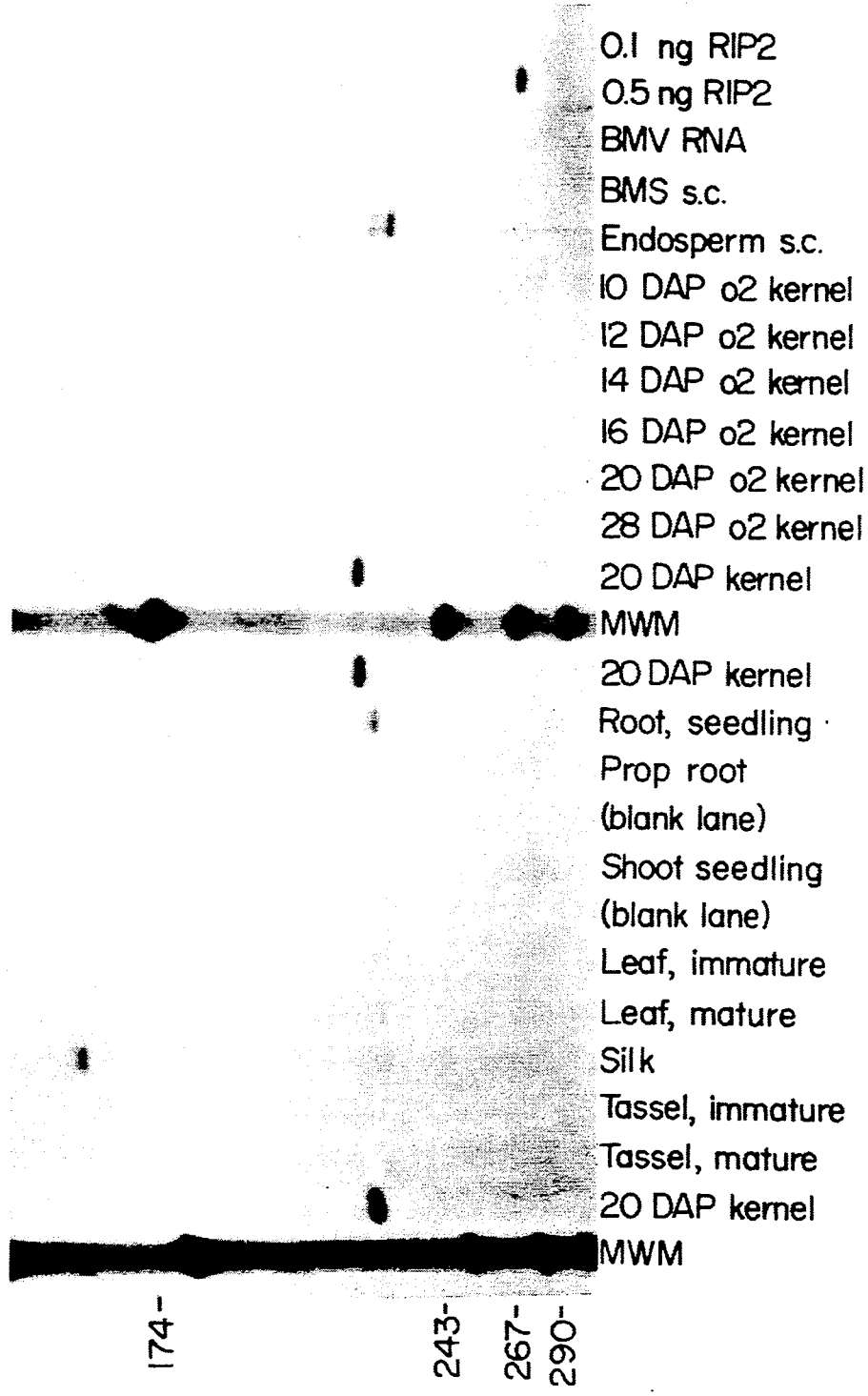

To optimize the assay, several experimental parameters were tested that might affect the specificity of extension products transcribed. The autoradiograph in FIG. 7 shows denaturing gel fractionation of primer extension products from positive control RNA (sections headed RIP2 and RIP1), negative control RNA (lanes tRNA and BMV), or maize RNA (lanes 20 DAP kernel, endosperm s.c., and BMS s.c.). The experimental variables are indicated above each lane. The extension product from the synthetic RIP2 RNA was predicted to be 275 nt based on the position of the restriction enzyme site at which the template plasmid for RNA synthesis was linearized. Using the RIP2 synthetic RNA for a template, the 45° C. primer extension reaction gave the strongest signal (RIP2 lane 45° C. 45 min). However, the relative amount of signal below the major extension products appeared to be greater in this lane than in the lane showing extension products from a 37° C. reaction (37° C. 60 min). A 55° C. primer extension reaction showed reduced amounts of the major extension products (RIP2 lane 55° C. 60 min). Therefore, based on the intensity of signal as well as the ratio of full length extension products to the smaller bands, the 37° C. 60 min primer extension reaction was considered to be the optimal reaction.

Synthetic RIP1 RNA (section headed RIP1) was also used as a substrate and the full length run off transcription product was predicted to be 245 nt. Of the three conditions tested, 45° C. 60 min, 45° C. 30 min, and 37° C. 45 min, the 37° C. reaction gave the optimal results based upon the same criteria discussed above. The specificity of the reaction for RIP RNA was demonstrated by primer extension reactions of control RNAs (tRNA and BMV) which showed no extension products.

Total RNA from maize kernels harvested at 20 DAP (lanes 20 DAP kernel) directed synthesis of a distinct extension product of approximately 210 nt. RNA from an endosperm suspension culture (Endosperm s.c.) showed two very closely migrating extension products, with the smaller of the two products comigrating with the products from kernel RNA. Reactions using RNA from BMS suspension cultures (BMS s.c.) contained no detectable RIP RNA as determined by the absence of extension products in that lane.

Once reaction conditions yielding specific primer extension products were established, RNAs from various parts of the plant were assayed for RIP RNA. The results of this experiment are presented in FIG. e with the sources of the RNA listed above the lanes. Primer extension reactions containing 0.1 and 0.5 ng of synthetic RNA from a RIP2 clone were included as controls and the resulting extension products are shown in the first two lanes (lanes 0.1 ng RIP2 and 0.5 ng RIP2). The presence of RIP RNA in roots was demonstrated by detection of a 216 nt band (lane Root, seedling). In addition to the lanes representing products from root RNA, the lanes showing products reverse transcribed from the RNA of leaf, silk, tassel, and endosperm suspension culture (lanes Leaf, immature; Leaf, mature; silk; tassel, mature; and Endosperm s.c.) also showed this 216 nt band. A slightly smaller band of 212 nt was visible in RNA isolated from developing kernels (lanes 20 DAP kernel, compare lanes 20 DAP kernel with Root, seedling). Additionally, the RNAs from 16 and 20 DAP opaque-2 kernels directed synthesis of the 212 nt extension products (lanes 16 DAP o2 kernel and 20 DAP o2 kernel). The only other lane showing the 212 nt extension product was that containing reaction products transcribed from RNA isolated from an endosperm culture (lane Endosperm s.c.). Only this reaction resulted in both the 212 and 216 nt bands, a result corresponding to that observed in FIG. 7.

The extension products (212 nt) from kernel RNA were believed to be transcribed from the RIP1 RNA which is present at high levels in kernels harvested at 20 DAP (Bass et. al., 1992). Consistent with this interpretation was the presence of the 212 nt products from the same RNAs shown to contain RIP1 RNA (ie., 16 and 20 DAP opaque-2 kernel RNA). The larger (216 nt) transcription products derived from reactions containing RNAs from root, silk, tassel, and endosperm culture are believed to result from RIP2 RNA. This assignment is consistent with the earlier observation that RNAs from these sources hybridized to the RIP2 RNA-specific probe RMA89 (FIG. 5).

EXAMPLE 10

RIP Activity of pRIP2-B6 RNA in vitro

The site-specific depurination of the large rRNA by RIPs can be monitored by gel electrophoresis of the purified RNA that has been treated with aniline. At an acidic pH, aniline induces strand scission at the point of depurination and generates a 3' terminal rRNA fragment of approximately 400 nt. To determine whether or not the lambdaRIP2 clone encoded a protein with RIP activity, rabbit reticulocyte translation extracts were programmed with synthetic RNA corresponding to the open reading frame region of RIP2.

Template plasmids (pPST3 and pPST7, described above) were linearized by digestion with Eco RI at a single site, and transcribed in vitro with T7 RNA Polymerase as instructed by the manufacturer (Epicentre Technologies, Madison, WI). The methods for purification and quantitation of synthetic RNAs are described above in Example 9. Aniline cleavage assays were performed on rabbit reticulocyte RNA from translation extracts as described by Bass et. al., supra, unless specified otherwise below. L-methionine was substituted for radiolabeled L-methionine. Micrococcal nuclease treatment was performed according to the instructions supplied with the lysate (Promega). Synthetic or BMV RNAs were added to 20 $\mu$g/mL. Gelonin (Calbiochem) was added to 0.1 $\mu$g/mL. Reactions were for 45 min. at 30° C.

Figure 9:
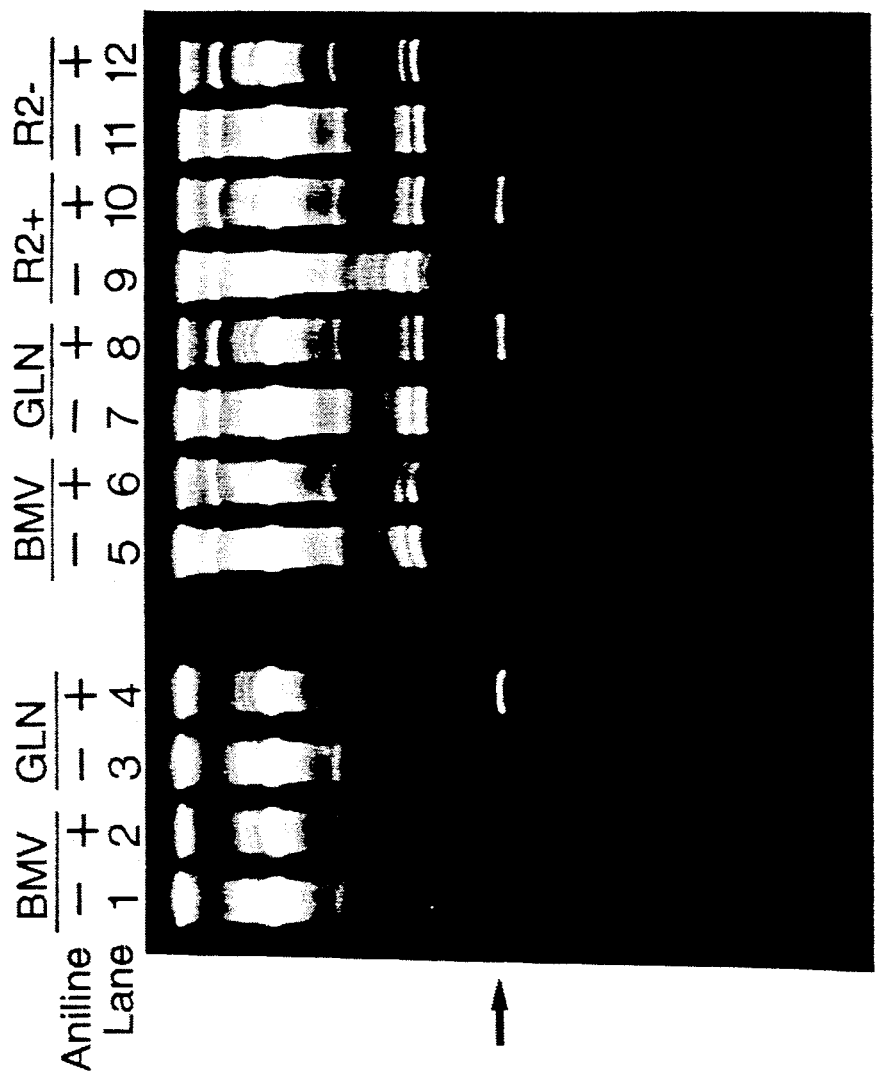

As shown in FIG. 9, RNA from translation extracts containing RIP2 coding strand RNA (lanes R2+) gave an aniline-dependent RNA fragment diagnostic for RIP activity (arrow). RNA from extracts plus either the RIP2 noncoding strand (lanes R2-) or BMVRNA (lanes BMV) did not show additional RNA fragments upon aniline treatment. For comparison, RNA from extracts treated with the commercially-available RIP, gelonin, showed the aniline-dependent RNA band (arrow).

In addition to the aniline-specific bands, several abundant RNA bands were observed (lanes 5–12). Their presence does not, however, affect the specificity of the RIP reaction assay. This is demonstrated by comparison of RNA from rabbit reticulocyte lysate that had not been treated with micrococcal nuclease (lanes 1–4). Rabbit reticulocyte lysate was incubated with control RNA (BMV lanes 1 and 2) and gelonin (GLN lanes 3 and 4). The band specific for RIP plus aniline treatment was the same size as that from lanes 8 and 10, which indicated the micrococcal nuclease treatment affected neither the specificity of the reaction nor the size of the 3' scission product. Additionally, this result indicated that the region of the large rRNA that is modified by RIPs was not a micrococcal nuclease hypersensitive site under the conditions of this experiment.

The foregoing examples are illustrative of the present invention, and are not to be construed as limiting thereof. The invention is defined by the following claims, with equivalents of the claims to be included therein.

---

That which is claimed is:

1. Isolated DNA encoding a ribosome-inactivating protein, said DNA being selected from the group consisting of:
   (a) isolated DNA having the sequence given herein as SEQ ID NO:1; and
   (b) isolated DNAs differing from the isolated DNA of (a) above in nucleotide sequence due to the degeneracy of the genetic code, and which encode a ribosome inactivating protein encoded by isolated DNA of (a) above.

2. Isolated DNA encoding a ribosome-inactivating protein having the sequence given herein as SEQ ID NO:1.

3. Isolated DNA according to claim 1, wherein said DNA encodes a Zer ribosome-inactivating protein.

4. A chimeric DNA comprising vector DNA and a DNA according to claim 1.

5. A chimeric DNA according to claim 4 further comprising a promoter region which activates transcription of said DNA.

* * * * *

UNITED STATES PATENT AND TRADEMARK OFFICE
CERTIFICATE OF CORRECTION

PATENT NO. : 5,332,808
DATED : July 26, 1994
INVENTOR(S) : Rebecca S. Boston, Henry W. Bass, Gregory R. O'Brian It is certified that error appears in the above-indentified patent and that said Letters Patent is hereby corrected as shown below:

Column 1, line 34, please correct "("RIPi")" to read --("RIP1")--.

Column 1, line 66, please remove "35".

Column 2, line 24, please correct "Sinai (Sin, 2.79)" to read -- SmaI (Sm, 2.79) --.

Column 2, line 43 & 44, please correct "RIPO-3" to read -- RIP-3 --.

Column 3, line 26, please correct "Tm-88°" to read -- Tm-8° --.

Column 3, line 39, please correct "RIP1(-1)" to read -- RIP1 RNA (-1) --.

Column 4, line 35, please remove -- 15 --.

Column 8, line 7, please correct "*tabacura*" to read -- *tabacum* --.

Column 8, line 32, please correct " 26 " to read -- A260 --.

Column 8, line 34, please correct " Mi " to read -- M1 --.

Column 8, lines 38, please correct " rain " to read -- min --.

UNITED STATES PATENT AND TRADEMARK OFFICE
CERTIFICATE OF CORRECTION

PATENT NO. : 5,332,808

DATED : July 26, 1994

INVENTOR(S) : Rebecca S. Boston, Henry W. Bass, Gregory R. O'Brian

It is certified that error appears in the above-indentified patent and that said Letters Patent is hereby corrected as shown below:

```
Column 9, line 12, please correct "SauA" to read
     -- Sau3A --.

Column 9, line 14, please correct "³²P" to read -- 32P --.

Column 9, lines 40 & 42, please correct "RiP2" to read
     -- RIP2 --.

Column 9, line 48, please correct "164-168" to read
     -- 165-168 --.

Column 10, line 63, please correct "eDNA" to read
     -- cDNA --.

Column 11, line 26, please correct "Map" to read
     -- MAP --.

Column 12, line 33, please add -- UV -- after by.

Column 12, line 64, please correct "(5.6)" to read
     -- (5,6) --.
```

Signed and Sealed this

Fifteenth Day of November, 1994

*Attest:*

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1934 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 990..1826

( x i ) SEQUENCE DESCRIPTION: SEQ ID NO:1:

-continued

```
GTGCCAAGCT TTGAAAGAAG GATGTCAAAA GGCATTGGTG ATTGAACAAA GGCAGTCAAG      60
AGCCATTGAA AGAAAGTTGT ATGTTGAGAG CACTAAGACA ACGGTCTTAC AGTGTACAAA     120
ATATATCACT GAATAGTTAT ATCTTACTTT TTTAGCACTT GAGCAATTAA ACTTTTAGTT     180
GTTCATTGTT ATAGTCGATA CCCAGATATC ATACAGTGTC TAATATGAAC ATTTAATTTT     240
CATGTAATCA TTATGCTCTA ACATTTTTC  CCAAATAATG TGCTGTTGCA ACGACGGGCA     300
TCGTACTAGT AAAGTATATA TATATATATA TATATAGACT TTTACCATTC AAAAAAATTT     360
GAGGGCCTCA ATTTTTGTTT CGCCCCGGGT CCATGAAACC TAGGGACCGG CCGTGTATAT     420
ATATGGTCTT CCCTTCACTA ACTATATAGA GACAGATCAC ATCGGAATAA AGAAATTTA      480
TAGACCAAAT CGGAAACCTA AAACCAAAA  ACCGAGCAAT TCGGTCTATT CGGTTTTAGT     540
TAGCAGGTTC AAAATGTCCG GTCCTACTAA TACTCAACAA TGATTAAGAA CCGATCTGCC     600
ATATTTAAA  AAAATTATGG ACCGGAATAA CACATAGCGA AAAGTTTAAG GAGCGAAAAT     660
ATTTTTTTTT CCTTGGCAAT TTGGACGGCA CGCGGAGACT GGCAGACCGC ATCCTCGTGA     720
AGCACGTTGT CCATGCCTGA AGAGAGTATT CTGTATTCGC AGTATTCCTG CATTTAAAAG     780
TTTGGTGAGC GAATCAATAA TTGGCATAAA TAATGCTACC GACGCATCAC CACATAGTAC     840
GTACCATAGT CATCCTTATC CTATCGAATT ACCTACATGC CCAACCCTCC CACTACATAT     900
ATCTGCAACG AGCGCATCGC CAATTCACAA TGCCAATTGC CAGCAACCCA TCCATACTTT     960
CAGCTGTTGA TACAAAAGA  GAAGAGAGA  ATG GCG GAG CCA AAC CCA GAG TTG    1013
                                Met Ala Glu Pro Asn Pro Glu Leu
                                 1               5

AGT GGT CTT ATT ACT CAA ACA AAG AAG AAA AAT ATA GTG CCA AAG TTC      1061
Ser Gly Leu Ile Thr Gln Thr Lys Lys Lys Asn Ile Val Pro Lys Phe
     10              15                  20

ACC GAA ATC TTC CCC GTG GAG GAC ACG GCC TAC CCT TAC AGC GCC TTC      1109
Thr Glu Ile Phe Pro Val Glu Asp Thr Ala Tyr Pro Tyr Ser Ala Phe
 25                  30                  35                  40

ATC ACC TCC GTC CGG AAA GAA GTG ATC AAA TAC TGC ACC AAC CAT ACA      1157
Ile Thr Ser Val Arg Lys Glu Val Ile Lys Tyr Cys Thr Asn His Thr
                 45                  50                  55

GGC ATC GTC CAG CCC GTG CTG CCG CTG GAG AAG AAT GTC CCC GAG CTC      1205
Gly Ile Val Gln Pro Val Leu Pro Leu Glu Lys Asn Val Pro Glu Leu
             60                  65                  70

TGG TTC TAC ACC GAG CTC AAA ACG AAG ACC AGG TCC ATC ACG CTC GCC      1253
Trp Phe Tyr Thr Glu Leu Lys Thr Lys Thr Arg Ser Ile Thr Leu Ala
         75                  80                  85

ATA CGT ATG GAC AAC CTC TAC CTG GTC GGC TTC AGG ACC CCC GGC GGG      1301
Ile Arg Met Asp Asn Leu Tyr Leu Val Gly Phe Arg Thr Pro Gly Gly
     90                  95                 100

GTG TGG TGG GAG TTC GGC AAG GAC GGC GAC ACC CAC CTC CTC GAC GAC      1349
Val Trp Trp Glu Phe Gly Lys Asp Gly Asp Thr His Leu Leu Asp Asp
105                 110                 115                 120

AAC GCC AAG TGG CTC GGC TTT GGC GGC CGG TAC CAG GAC CTC ATC GGC      1397
Asn Ala Lys Trp Leu Gly Phe Gly Gly Arg Tyr Gln Asp Leu Ile Gly
                125                 130                 135

AGT AAG GGC CTG GAG ACC GTC ACC ATG GGC CGT GCC GAA ATG ACC ACG      1445
Ser Lys Gly Leu Glu Thr Val Thr Met Gly Arg Ala Glu Met Thr Thr
            140                 145                 150

GCC GTC AAC TAC CTG GCG AAG AAG ACG ACG ACG ACA CTA GCA GAG GCG      1493
Ala Val Asn Tyr Leu Ala Lys Lys Thr Thr Thr Thr Leu Ala Glu Ala
        155                 160                 165

GCG GAG GAG GAG GAG GAG CTG CTG CTG CTG CAG GCA GCG GCT GAC CCC      1541
Ala Glu Glu Glu Glu Glu Leu Leu Leu Leu Gln Ala Ala Ala Asp Pro
170                 175                 180

AAA GCC GAG GAG AAG AGC AAC CTG GCG AAG CTA GTG ATC ATG GTA TGC      1589
```

| | | | | | | | | | | | | | | | |
|---|---|---|---|---|---|---|---|---|---|---|---|---|---|---|---|
| Lys | Ala | Glu | Glu | Lys | Ser | Asn | Leu | Ala | Lys | Leu | Val | Ile | Met | Val | Cys |
| 185 | | | | | 190 | | | | 195 | | | | | | 200 |

| GAG | GGG | CTG | CGG | TTC | TTC | ACC | GTG | TCC | CGC | AAG | GTA | GAC | GAG | GGG | TTC | 1637 |
|---|---|---|---|---|---|---|---|---|---|---|---|---|---|---|---|---|
| Glu | Gly | Leu | Arg | Phe | Phe | Thr | Val | Ser | Arg | Lys | Val | Asp | Glu | Gly | Phe | |
| | | | | 205 | | | | | 210 | | | | | 215 | | |

| AAG | AAG | CCG | CAA | GCG | GTG | ACC | ATA | TCG | GCG | CTG | GAG | GGG | AAG | CAG | GTG | 1685 |
|---|---|---|---|---|---|---|---|---|---|---|---|---|---|---|---|---|
| Lys | Lys | Pro | Gln | Ala | Val | Thr | Ile | Ser | Ala | Leu | Glu | Gly | Lys | Gln | Val | |
| | | | 220 | | | | | 225 | | | | | 230 | | | |

| CAG | AAA | TGG | GAC | AGG | ATC | TCG | AAA | GCC | GTC | TTC | AGG | TGG | GCC | GTC | GAC | 1733 |
|---|---|---|---|---|---|---|---|---|---|---|---|---|---|---|---|---|
| Gln | Lys | Trp | Asp | Arg | Ile | Ser | Lys | Ala | Val | Phe | Arg | Trp | Ala | Val | Asp | |
| | | | 235 | | | | 240 | | | | | 245 | | | | |

| CCG | ACC | GCT | GAG | ATC | CCC | GAC | ATG | AAG | GAT | CTT | GGC | ATC | AAA | GAT | AAA | 1781 |
|---|---|---|---|---|---|---|---|---|---|---|---|---|---|---|---|---|
| Pro | Thr | Ala | Glu | Ile | Pro | Asp | Met | Lys | Asp | Leu | Gly | Ile | Lys | Asp | Lys | |
| | | 250 | | | | | 255 | | | | 260 | | | | | |

| AAC | GCA | GCA | GCG | CAG | ATC | GTT | GCG | CTC | GTT | AAG | GAC | CAA | AAC | TAGTACTGCT | 1833 |
|---|---|---|---|---|---|---|---|---|---|---|---|---|---|---|---|
| Asn | Ala | Ala | Ala | Gln | Ile | Val | Ala | Leu | Val | Lys | Asp | Gln | Asn | | |
| 265 | | | | 270 | | | | | 275 | | | | | | |

GCTACTACTA CGTATGAGAA CAAGGAGGAG TTCTCTGATG ATGATACACA CATCAAGACT     1893

TGTTTGTTGC TCTACTTCCA CGTGGTACAG TAGCAGTATA C     1934

( 2 ) INFORMATION FOR SEQ ID NO:2:

( i ) SEQUENCE CHARACTERISTICS:
        ( A ) LENGTH: 278 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ala | Glu | Pro | Asn | Pro | Glu | Leu | Ser | Gly | Leu | Ile | Thr | Gln | Thr | Lys |
| 1 | | | | 5 | | | | | 10 | | | | | 15 | |
| Lys | Lys | Asn | Ile | Val | Pro | Lys | Phe | Thr | Glu | Ile | Phe | Pro | Val | Glu | Asp |
| | | | 20 | | | | | 25 | | | | 30 | | | |
| Thr | Ala | Tyr | Pro | Tyr | Ser | Ala | Phe | Ile | Thr | Ser | Val | Arg | Lys | Glu | Val |
| | | | 35 | | | | 40 | | | | | 45 | | | |
| Ile | Lys | Tyr | Cys | Thr | Asn | His | Thr | Gly | Ile | Val | Gln | Pro | Val | Leu | Pro |
| | 50 | | | | | 55 | | | | | 60 | | | | |
| Leu | Glu | Lys | Asn | Val | Pro | Glu | Leu | Trp | Phe | Tyr | Thr | Glu | Leu | Lys | Thr |
| 65 | | | | | 70 | | | | | 75 | | | | | 80 |
| Lys | Thr | Arg | Ser | Ile | Thr | Leu | Ala | Ile | Arg | Met | Asp | Asn | Leu | Tyr | Leu |
| | | | | 85 | | | | | 90 | | | | | 95 | |
| Val | Gly | Phe | Arg | Thr | Pro | Gly | Gly | Val | Trp | Trp | Glu | Phe | Gly | Lys | Asp |
| | | | | 100 | | | | | 105 | | | | | 110 | |
| Gly | Asp | Thr | His | Leu | Leu | Asp | Asp | Asn | Ala | Lys | Trp | Leu | Gly | Phe | Gly |
| | | | 115 | | | | | 120 | | | | | 125 | | |
| Gly | Arg | Tyr | Gln | Asp | Leu | Ile | Gly | Ser | Lys | Gly | Leu | Glu | Thr | Val | Thr |
| | | | 130 | | | | | 135 | | | | 140 | | | |
| Met | Gly | Arg | Ala | Glu | Met | Thr | Thr | Ala | Val | Asn | Tyr | Leu | Ala | Lys | Lys |
| 145 | | | | | 150 | | | | | 155 | | | | | 160 |
| Thr | Thr | Thr | Thr | Leu | Ala | Glu | Ala | Ala | Glu | Glu | Glu | Glu | Glu | Leu | Leu |
| | | | | 165 | | | | | 170 | | | | | 175 | |
| Leu | Leu | Gln | Ala | Ala | Ala | Asp | Pro | Lys | Ala | Glu | Glu | Lys | Ser | Asn | Leu |
| | | | | 180 | | | | | 185 | | | | | 190 | |
| Ala | Lys | Leu | Val | Ile | Met | Val | Cys | Glu | Gly | Leu | Arg | Phe | Phe | Thr | Val |
| | | | 195 | | | | | 200 | | | | | 205 | | |
| Ser | Arg | Lys | Val | Asp | Glu | Gly | Phe | Lys | Lys | Pro | Gln | Ala | Val | Thr | Ile |
| | 210 | | | | | 215 | | | | | 220 | | | | |
| Ser | Ala | Leu | Glu | Gly | Lys | Gln | Val | Gln | Lys | Trp | Asp | Arg | Ile | Ser | Lys |

```
                    225                        230                          235                              240
Ala  Val  Phe  Arg  Trp  Ala  Val  Asp  Pro  Thr  Ala  Glu  Ile  Pro  Asp  Met
                         245                        250                          255
Lys  Asp  Leu  Gly  Ile  Lys  Asp  Lys  Asn  Ala  Ala  Ala  Gln  Ile  Val  Ala
                    260                        265                          270
Leu  Val  Lys  Asp  Gln  Asn
               275
```

( 2 ) INFORMATION FOR SEQ ID NO:3:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..54

( x i ) SEQUENCE DESCRIPTION: SEQ ID NO:3:

```
ACG  ACA  CTA  GCA  GAG  GCG  GCG  GAG  GAG  GAG  GAG  GAG  CTG  CTG  CTG  CTG      48
Thr  Thr  Leu  Ala  Glu  Ala  Ala  Glu  Glu  Glu  Glu  Glu  Leu  Leu  Leu  Leu
 1                   5                        10                       15

CAG  GCA                                                                            54
Gln  Ala
```

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Thr  Thr  Leu  Ala  Glu  Ala  Ala  Glu  Glu  Glu  Glu  Glu  Leu  Leu  Leu  Leu
 1                   5                        10                       15

Gln  Ala
```

( 2 ) INFORMATION FOR SEQ ID NO:5:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..75

( x i ) SEQUENCE DESCRIPTION: SEQ ID NO:5:

```
ATG  GCG  ACA  CTG  GAG  GAG  GAG  GAG  GTG  AAG  ATG  CAG  ATG  CAG  ATG  CCG      48
Met  Ala  Thr  Leu  Glu  Glu  Glu  Glu  Val  Lys  Met  Gln  Met  Gln  Met  Pro
 1                   5                        10                       15

GAG  GCC  GCT  GAT  CTG  GCG  GCG  GCG  GCA                                         75
Glu  Ala  Ala  Asp  Leu  Ala  Ala  Ala  Ala
               20                       25
```

( 2 ) INFORMATION FOR SEQ ID NO:6:

( i ) SEQUENCE CHARACTERISTICS:
        ( A ) LENGTH: 25 amino acids (B) TYPE: amino acid
(D) TOPOLOGY: linear (ii) MOLECULE TYPE: protein (xi) SEQUENCE DESCRIPTION: SEQ ID NO:6:

Met Ala Thr Leu Glu Glu Glu Glu Val Lys Met Gln Met Gln Met Pro
 1           5                   10                  15
Glu Ala Ala Asp Leu Ala Ala Ala Ala
            20              25